United States Patent [19]
Oakley et al.

[11] Patent Number: 5,335,663
[45] Date of Patent: Aug. 9, 1994

[54] LAPAROSCOPIC PROBES AND PROBE SHEATHS USEFUL IN ULTRASONIC IMAGING APPLICATIONS

[75] Inventors: Clyde G. Oakley, Englewood; Lawrence J. Busse; Dennis R. Dietz, both of Littleton; John E. Shishilla, Aurora; Joseph V. Ranalletta, Englewood, all of Colo.

[73] Assignee: Tetrad Corporation, Englewood, Colo.

[21] Appl. No.: 989,515

[22] Filed: Dec. 11, 1992

[51] Int. Cl.$^5$ ................................................ A61B 8/12
[52] U.S. Cl. ................................ 128/662; 128/662.03; 128/662.05
[58] Field of Search .............. 128/662.06, 662.03, 128/660.03, 662.05, 661.01, 660.01, 4, 24 AA, 660.07; 606/10, 13, 39, 40

[56] References Cited

U.S. PATENT DOCUMENTS

| | | | |
|---|---|---|---|
| 4,155,258 | 5/1979 | Engeler et al. | 73/626 |
| 4,417,583 | 11/1983 | Bechai et al. | 128/4 |
| 4,593,699 | 6/1986 | Poncy et al. | 128/662.03 |
| 4,646,722 | 3/1987 | Silverstein et al. | 128/4 |
| 4,722,345 | 2/1988 | Ueno et al. | 128/660.09 |
| 4,756,313 | 7/1988 | Terwilliger | 128/660 |
| 4,763,662 | 8/1988 | Yokoi | 128/660 |
| 4,779,624 | 10/1988 | Yokoi | 128/660.06 |
| 4,802,487 | 2/1989 | Martin et al. | 128/662.06 |
| 4,815,470 | 3/1989 | Curtis et al. | 128/662.03 |
| 4,817,616 | 4/1989 | Goldstein | 128/662.06 |
| 4,825,850 | 5/1989 | Opie et al. | 128/4 |
| 4,880,011 | 11/1989 | Imade et al. | 128/662.06 |
| 4,907,395 | 3/1990 | Opie et al. | 53/434 |
| 4,951,677 | 8/1990 | Crowley et al. | 128/662.06 |
| 4,997,084 | 3/1991 | Opie et al. | 206/364 |
| 5,002,059 | 3/1991 | Crowley et al. | 128/662.06 |
| 5,020,539 | 6/1991 | Yokoi et al. | 128/662.06 |
| 5,025,778 | 6/1991 | Silverstein et al. | 128/4 |
| 5,054,491 | 10/1991 | Saito et al. | 128/662.06 |
| 5,070,879 | 12/1991 | Herres | 128/660.08 |
| 5,088,178 | 2/1992 | Stolk | 29/453 |
| 5,090,414 | 2/1992 | Takano | 128/662.05 |
| 5,105,819 | 4/1992 | Wollschläger et al. | 128/662.06 |
| 5,117,831 | 6/1992 | Jang et al. | 128/662.06 |
| 5,121,749 | 6/1992 | Nassi et al. | 128/692 |
| 5,125,411 | 6/1992 | Yokoi et al. | 128/662.06 |
| 5,131,393 | 7/1992 | Ishiguro et al. | 128/660.09 |
| 5,131,396 | 7/1992 | Ishiguro et al. | 128/662.03 |
| 5,135,001 | 8/1992 | Sinofsky et al. | 128/662.06 |
| 5,150,715 | 4/1993 | Ishiguro et al. | 128/662.06 |
| 5,190,045 | 3/1993 | Frazin | 128/662.06 |
| 5,207,672 | 5/1993 | Roth et al. | 128/660.03 |

OTHER PUBLICATIONS

General Purpose Pro/Covers TM, Advertising Brochure, Civco, date unknown.
AI 5200 Ultrasound Imaging System, Advertising Brochure, Acoustic Imaging, Tempe, AZ, date unknown.
OR340 Intraoperative Ultrasound System, Advertising Brochure, Codman & Shurtleff, Inc., a Johnson & Johnson Company, Randolph, Mass., date unknown.

Primary Examiner—William E. Kamm
Assistant Examiner—George Manuel
Attorney, Agent, or Firm—Sheridan Ross & McIntosh

[57] ABSTRACT

The invention relates to a medical ultrasonic imaging probe, such as may be used in laparoscopic surgery. A probe is provided having both forward viewing and side viewing ultrasonic capabilities. An apparatus is provided for manipulating and orienting video ultrasound images on a video monitor according to the position of the probe. A probe is also provided having both an ultrasonic device and a surgical tool, such as an electrocautery hook for excising and/or cauterizing tissue, that can be closely monitored by the ultrasonic device. Also provided is an ultrasonic probe having lumens for placing ultrasonically transmissive medium adjacent to ultrasonic transducers. A removable, rigid sheath is provided to fit over a laparoscopic probe. Removable sheath that includes a lumen for transmission of surgical tools and the like, an inner chamber containing ultrasonically transmissive medium and sealed with a breakable membrane, a balloon that can be inflated with ultrasonically transmissive medium, and lumens for injecting ultrasonically transmissive medium in the vicinity of a probe's ultrasonic device of a probe inserted into the sheath are disclosed.

35 Claims, 9 Drawing Sheets

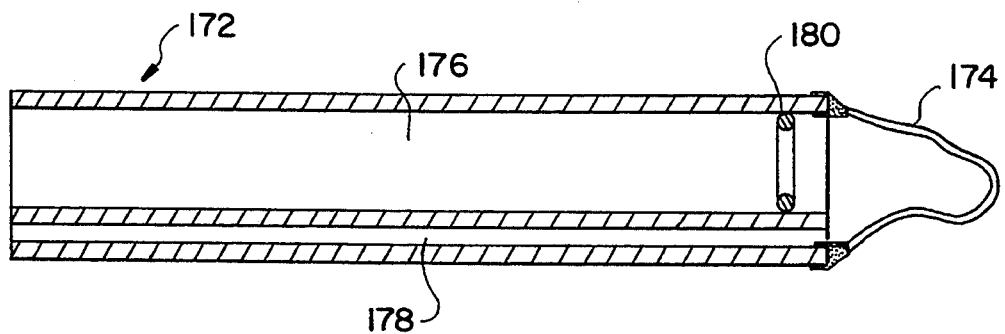
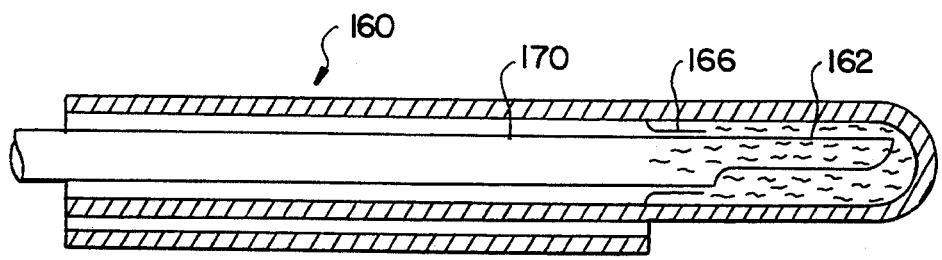
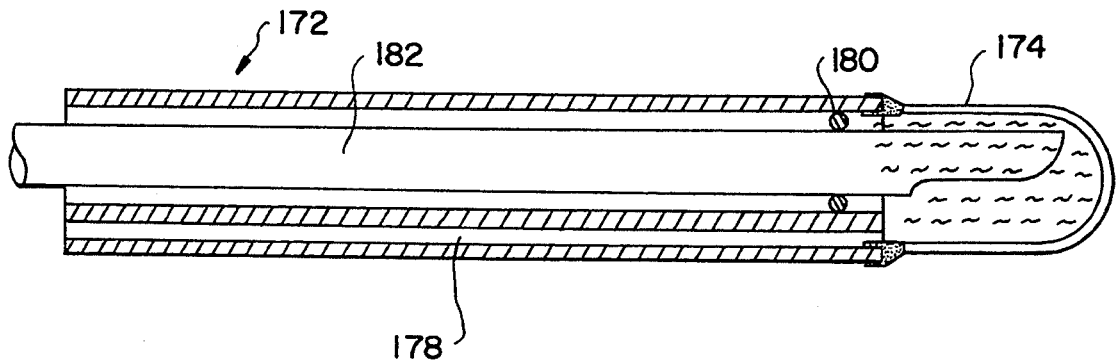

LAPAROSCOPIC PROBES AND PROBE SHEATHS USEFUL IN ULTRASONIC IMAGING APPLICATIONS

FIELD OF THE INVENTION

The present invention relates to ultrasonic imaging apparatus that are particularly suited for use in laparoscopic surgery.

BACKGROUND OF THE INVENTION

Ultrasonic imaging has found several applications in the medical field, especially to view internal anatomical tissue and structures. One well known application, for example, is to use a hand held ultrasonic probe to image a developing fetus during pregnancy. Ultrasonic imaging has also found application in laparoscopic surgery, such as in the performance of biopsies and excision of internal organs or other tissue.

Laparoscopic surgery involves the use of small diameter tools that are inserted into a patient's body cavity through a small hole in the abdominal wall. The hole is made by puncturing the abdominal wall with a sharp edged instrument called a trocar. A small working tube, called a cannula, is then inserted into the hole to hold it open. Through the internal passageway of the cannula, often referred to as a surgical port, are passed the necessary instruments into the body cavity to perform desired surgical operations.

Normally, the trocar and cannula are configured in a single structure. Also, the cannula is usually fitted inside with some type of sealing apparatus, such as, for example, a flapper valve that can be forced open by a tool entering through the cannula, and which springs closed to seal the internal passageway through the cannula when not in use. The cannula can also be fitted with annular sealing devices for sealing between a probe inserted through the cannula and the inside wall of the cannula. Such a means for sealing the passageway of the cannula prevents contaminants from the outside environment from invading the body cavity, thereby reducing the possibility of infection.

Various probes have been used to aid laparoscopic surgical operations. For example, optical probes are often used to view the outer surfaces of internal organs. Also, ultrasonic probes have been used to assist in viewing the internal structures of organs to obtain information that may be necessary for performance of certain surgical operations. For example, a surgeon might need to be able to identify and distinguish the cystic duct from the common duct in the gall bladder/liver to perform certain procedures.

A variety of ultrasonic probes have been used in laparoscopic procedures. One type of probe has a single transducer that is mechanically moved through an arc to transmit or receive ultrasonic signals over a pie-shaped area. Such a mechanical sector scanner can be positioned on a probe to image in either a forward or a side direction. A second type of ultrasonic probe that is used to transmit or receive ultrasonic signals over an area contains several transducer elements arranged in an array. One type of array probe that has been used contains several transducers arranged in a line along the side of a cylindrically shaped probe. Such a linear array provides side imaging capability. Another type of array probe aligns the array of transducer elements along a curve at or near the end of a probe to provide forward looking capability. Such a curved array transmits and receives ultrasonic signals over a pie-shaped area like the mechanical sector scanner. Although working well for forward viewing that is useful as a general directional and positional guide, curved arrays are not well suited for imaging near the probe, as is often desirable during surgery, because of a limited field of imaging in the region near the curved array.

During laparoscopic surgical operations, ultrasonic imaging in a forward direction beyond the end of the probe is often required. Ultrasonic imaging to the side of the probe, however, is also often required. The ability to do both forward and side imaging are desirable during some operations. For example, forward imaging can be used to determine when a probe is at the location into the body cavity for side imaging organs or other tissue of interest which cannot be adequately viewed with a forward imaging probe.

Typically, when a need exists for both forward and side imaging, two separate probes are used, one for forward imaging and one for side imaging. For example, a forward imaging probe might first be inserted so that a surgeon can determine the proper distance into the body cavity at which the operation is generally to be performed and possibly also to locate an organ or other tissue of interest. The forward imaging probe is then removed and a side imaging probe is inserted to obtain a better view of the organ or other tissue of interest in preparation for a medical operation that is to be performed on the tissue, such as excising tissue or taking a biopsy sample. The use of two probes, however, is awkward. It is difficult for a surgeon performing a complex operation to mentally reorient between the forward and side looking images. Also, assuring proper repositioning of the probe at the proper distance into the body cavity can present a problem.

One attempt to provide some degree of both forward and side looking capability in a single probe has been to place a linear array at some acute angle relative to the longitudinal axis of the probe. Such an angled array, however, provides limited imaging capability in either the forward or the side directions, and is, therefore, of limited practical utility.

Another attempt to provide some degree of both forward and side looking capability in a signal probe has used a mechanically scanned ultrasonic transducer. These probes, like the probes using the angled array, have proved to be of limited practical utility due to their limited imaging capability in the forward and side directions. Moreover, the moving parts associated with mechanical scanners render the probes more susceptible to malfunction.

Based on the foregoing, there is a need for an ultrasonic probe that addresses the noted deficiencies of presently known probes in providing both forward and side imaging capability.

Presently, ultrasonic images produced by ultrasonic medical probes are displayed on a video monitor with a fixed frame of reference. The image is typically displayed on the monitor from top to bottom, with the distance away from the ultrasonic probe increasing going down the screen. Therefore, tissue nearest the ultrasonic probe is displayed at the top of the monitor and tissue farthest from the probe appears at the bottom of the monitor.

A surgeon, or other medical professional, viewing the ultrasound image must mentally translate the image as displayed on the monitor to a frame of reference in the patient's body, thereby orienting the image in order to properly locate organs or other tissue of interest. Also, when the probe is moved from one position to another, or rotated to image in a different plane, the surgeon must also mentally reorient that new image relative to the old image. For example, if the surgeon is viewing a first ultrasonic image with the probe in a first position looking sideways and then rotates the probe counterclockwise to produce a second image, the surgeon must mentally translate the second image counterclockwise from the first image to properly conceptualize the patient's anatomy. These mental translations and orientations of images can be difficult to make as well as potentially distracting during complex surgical operations.

Consequently, there exists a need to provide the surgeon with an ultrasonic image that reduces the mental image translations that the surgeon must presently make each time the probe is moved to obtain a new image.

Many laparoscopic surgical operations require cutting, or excision, of internal tissue. The tissue to be cut as well as other internal structures must be located and properly identified prior to performing the cutting operation. For example, it may be necessary to locate and identify the common duct that runs through the liver so that a subsequent cutting operation on the liver will not nick or sever the duct.

Presently known methods for performing cutting operations during laparoscopic surgery use techniques for locating and identifying tissue that present significant potential for cutting the wrong tissue. For instance, one method for locating, identifying, and cutting tissue involves inserting an ultrasonic probe into the patient's body cavity to locate and identify the tissue to be cut and internal structures to be avoided. The ultrasonic probe is then removed and a surgical instrument is inserted and positioned to perform the cutting based on the information obtained from the ultrasonic probe. Positioning the surgical tool to properly perform the desired cut, however, based upon the information provided by the ultrasonic probe may be difficult, and it is possible that an improper cut can be made.

Therefore, a need exists for reducing the possibility that an improper cut or excision is made.

One problem often encountered with performing ultrasonic scans during laparoscopic operations is establishing good ultrasonic contact between ultrasonic transducers and tissue, the underlying structure of which is to be imaged. Good ultrasonic images can be produced only if adequate ultrasonic contract, often referred to as coupling, can be made between the tissue and ultrasonic transducers. Obtaining such ultrasonic contact is often difficult. For example, an ultrasonic device may be on the side of a probe, but only the tip of the probe can be contacted with the tissue of interest. Or, for example, it may be possible to contact the ultrasonic device and the tissue of interest, but in so doing the tissue is physically distorted and, therefore, the ultrasound image produced may be misleading.

One approach that has been used to establish ultrasonic contact with tissue is to fill the body cavity space in which the tissue resides with an ultrasonically transmissive fluid, such as water. However, this technique results in large amounts of transmissive fluid invading the body cavity. Transmissive fluids placed in the body cavity must normally be removed following the ultrasonic imaging operation. Assuring that large amounts of transmissive fluid have been completely removed from the body cavity can be troublesome.

Another problem with laparoscopic probes is that they are difficult to sterilize. One attempt to resolve the sterilization problem has been to place a sterile disposable cover, or sheath, over the laparoscopic probe prior to insertion of the probe into a body cavity. After removal of the probe, the sheath is discarded. As a consequence, the need for extensive sterilization of the probe is reduced.

One type of sheath that has been used to cover laparoscopic probes is a loose fitting, thin-walled, highly flexible prophylactic sheath made of an elastomeric-type material, such as latex rubber. One problem with the loose fitting prophylactic sheath however, is that it tends to catch and bind in the seals and/or a flapper valve in the cannula thereby inhibiting insertion and extraction of the probe. In extreme cases, the prophylactic sheath may tear, thereby defeating the very purpose of the sheath in providing a sterilized surface.

Another type of sheath that has been used is a thin-walled, tightly fitting, highly flexible sheath made of elastomeric-type material, such as latex rubber. The sheath is fitted on the probe by first inflating the sheath, like a balloon, and then inserting the probe into the inflated sheath. The sheath is then deflated to tightly fit around the probe. Because of the thin-walled, highly flexible nature of the sheath, however, there is still potential for binding in the cannula. Also, the procedure of fitting the sheath onto a probe is time consuming and awkward in the surgical environment. One related problem with using the sheaths just discussed, is assuring that an ultrasonically transmissive circuit is established between the ultrasonic device and the sheath. Currently, ultrasonic coupling between the ultrasonic device and the sheath is established by coating the probe with an ultrasonically transmissive fluid before covering the probe with a sheath. This procedure, however, is inconvenient, time consuming and awkward in the environment of an operating room.

Based on the foregoing, there is a need for establishing an ultrasonic device that can ultrasonically couple the transducer to the tissue of interest that avoids or reduces the problems associated with using large amounts of ultrasonically transmissive material to establish the requisite coupling.

SUMMARY OF THE INVENTION

In one embodiment, the present invention provides an ultrasonic imaging probe having both forward and side imaging capabilities on a single probe. The probe comprises a carrier and an array of ultrasonic transducers capable of imaging in a forward direction beyond the end of the end portion of the probe that is inserted into the patient's body. The ultrasonic array includes a first array portion that includes at least one ultrasonic transducer oriented to image at an acute angle relative to the longitudinal axis of the carrier such that the transducer images in a forward direction beyond the end of the probe. The array also includes a second portion having a plurality of ultrasonic transducers arranged in a substantially linear fashion and substantially parallel to the longitudinal axis of the carrier for side imaging.

In a further embodiment, the first array portion includes a plurality of transducers that are oriented so as to define a substantially planar curve, i.e., a curve that lies substantially in a single plane. In one embodiment, the planar curve has a large radius of curvature that extends over an acute included angle, thereby facilitating manufacture of the probe by making electrical connections to individual transducer elements easier to make. Alternatively the planar curve can have an increasing radius of curvature. By having a large radius of curvature, thereby decreasing the angle in which the curve is included, or by having an increasing radius of curvature, additional room is provided to make electrical connections to individual elements over the length of the curve. This can be particularly advantageous when the radius of the carrier is very small, such as with instruments used in laparoscopic surgery.

In a still further embodiment, the carrier of the probe is substantially cylindrical over much of its length, with the substantially circular cross section defining the areal boundary, perpendicular to the longitudinal axis, within which all portions of the probe must lie. In one embodiment, the transducer elements of the second array portion, arranged substantially in a line parallel with the longitudinal axis, are recessed relative to the areal boundary, thereby permitting other surgical tools, such as a biopsy needle, to be located within or passed through the recess. Moreover, those other surgical tools can be positioned within the imaging field of the linear portion of the array, thereby allowing a surgeon to simultaneously obtain an image of both the body tissue of interest and the surgical tool.

Another embodiment of the invention provides an ultrasonic imaging apparatus that addresses the mental translations and reorientations that surgeons must make with respect to the display of present ultrasonic images. The ultrasonic imaging apparatus includes an ultrasonic probe with at least one ultrasonic element that transmits a first electrical signal, representative of a received ultrasonic signal, a position sensor that produces a second electrical signal representative of the position of the probe, a processor for constructing a video image of the ultrasonic signal for display on a video monitor from the first electrical signal and manipulating the video image using the second electrical signal to reflect the orientation of the ultrasound image. For example, a first video image could be displayed on a video monitor representing an ultrasound image produced at a first position with a side imaging ultrasound probe. The probe could then be rotated counterclockwise to a second side imaging position. The second video image is rotated counterclockwise on the video monitor relative to the first video image thereby relieving the surgeon from having to make the mental adjustment in the image. In one embodiment, both a rotational position sensor and a translational position sensor are provided so that both rotations and translations of images can be effected.

Yet another embodiment includes a device for establishing a reference point for the position sensor that relates to a patient's body so that the ultrasound image displayed on a video monitor can be oriented to the patient. For example, if the reference point is the patient's head, the position sensor can produce data that allows a video image to be constructed in which the top of the video monitor corresponds to the patient's head and the bottom of the video monitor corresponds to the patients feet, regardless of the direction in which the ultrasonic probe is imaging.

One embodiment of the invention is directed to the problem locating or identifying the tissue of interest and then performing a cutting or other surgical operation. In an embodiment, the invention provides a laparoscopic probe that includes both a surgical device for cutting and/or cauterizing tissue and an ultrasonic device with a field of imaging that either includes the surgical device or is immediately adjacent to the surgical device. Because the surgical device is integral with the probe containing the ultrasonic device and is proximately located to the ultrasonic device, the surgeon is less likely to make improper cuts. In one embodiment, the surgical device includes an electrocautery hook that is positioned within or adjacent to the ultrasonic field of imaging of an ultrasonic array. Using the ultrasonic image, a surgeon can locate and identify the proper tissue for cutting as well as the internal structures that are not to be cut. After locating the proper tissue, the surgeon can activate the electrocautery hook and, because of the overlapping or immediately adjacent field of imaging, can closely control the precise position at which the cut is made.

A further embodiment of the present invention addresses the need to establish ultrasonic contact between an ultrasonic device and tissue of interest. The apparatus comprises a carrier, an ultrasonic device mounted on the carrier, and a device for use in injecting an ultrasonically transmissive medium adjacent to the ultrasonic device. The transmissive medium is placed in the vicinity of the ultrasonic device for the purpose of establishing an ultrasonic circuit, or bridge, with the tissue that is located in the field of view of the ultrasonic device.

In one embodiment, a high viscosity fluid is used as the transmissive medium. High viscosity fluids have the advantage that the medium has a reduced tendency, relative to lower viscosity fluids, to disperse or flow away from an area immediately adjacent to the ultrasonic device. Consequently, a relatively small amount of such high viscosity fluid can be used to provide the necessary ultrasonic contact for imaging the tissue of interest. The result is that a relatively small amount of transmissive medium is used which is relatively easy to remove from the body following ultrasonic imaging. Ease of removal is facilitated by the small amount of medium and an increased tendency of high viscosity medium to remain in the vicinity of the ultrasonic device. In one embodiment, the transmissive medium adheres to the outer surfaces of the carrier and ultrasonic device and does not disperse or flow away from that immediate vicinity.

One embodiment of the present invention provides a disposable sheath for covering a probe that is to be inserted into a patient's body cavity. In one embodiment, the sheath is a rigid structure that substantially reduces, or eliminates, any problem with binding of the sheath in the cannula as has been experienced with the thin walled, highly flexible, elastomeric-type sheaths of the prior art.

Another embodiment of the sheath includes a chamber within the sheath. The chamber contains an ultrasonically transmissive medium and is sealed with a breakable membrane. When a probe is inserted into the sheath, the probe breaks the membrane and the ultrasonic device of the probe enters the chamber containing the ultrasonically transmissive medium. An ultrasonic circuit is thereby established between the ultrasonic device and the sheath.

Another embodiment of the sheath includes an inflatable balloon at or near a first terminal end of the sheath that is inserted into the patient's body cavity. The balloon can be inflated with an ultrasonically transmissive medium to establish an ultrasonic circuit between an ultrasonic device of the probe inserted into the sheath and tissue to be ultrasonically scanned.

Another embodiment of the sheath is shaped to establish a desired orientation between the ultrasonic probe and the sheath. Orientation is such that the ultrasonic device of the probe is always adjacent to one or more lumens through which ultrasonically transmissive medium can be transmitted to and injected immediately adjacent the sheath in the direction of the ultrasonic beam. An ultrasonic circuit between the sheath and tissue of interest is established by the excreted medium.

BRIEF DESCRIPTION OF THE DRAWINGS

FIG. 12 shows the sheath of FIG. 11 in which the sealing membrane has been broken and a probe has been inserted into the chamber;

FIG. 13 shows another embodiment of the sheath having a balloon on the end that can be inflated with an ultrasonically transmissive medium through a lumen in the sheath;

FIG. 14 shows the sheath of FIG. 13 with the balloon inflated with ultrasonically transmissive medium and in which an ultrasonic probe has been inserted.

DETAILED DESCRIPTION

In one aspect, the present invention is an ultrasonic probe that provides ultrasonic imaging both in a forward direction past the end of the probe that is inserted into a patient's body and also to the side of the probe. The probe is particularly suited for use in laparoscopic surgical operations.

Figure 1A:
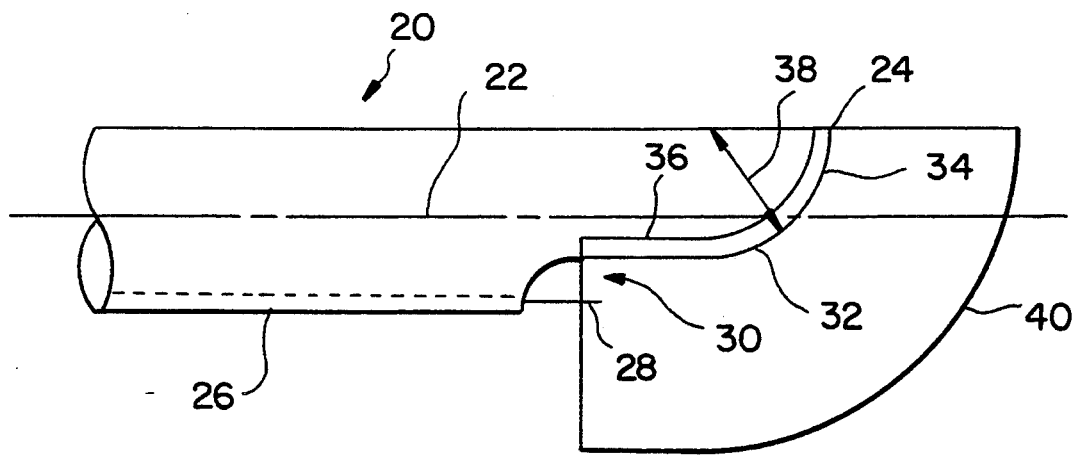
FIGS. 1A and 1B show a side view and a top view of a probe containing a 90° curved first array portion and a linear second array portion of an ultrasonic transducer array, which second array portion is recessed to allow for passage of a surgical tool, such as a biopsy needle.
Figure 1B:
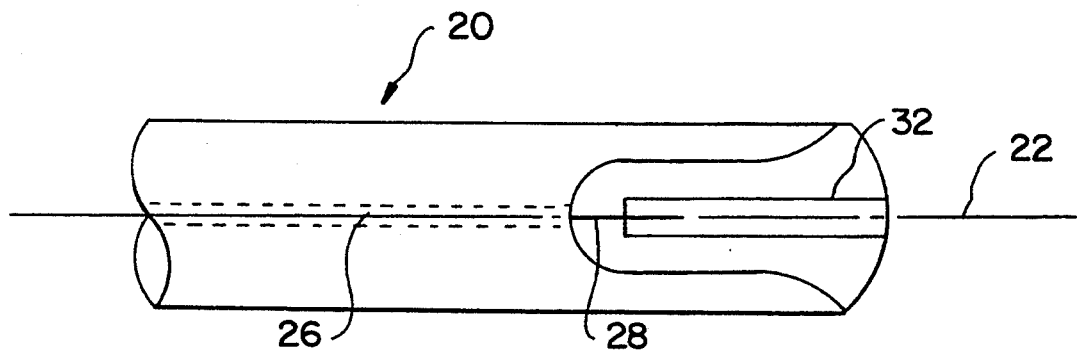

FIGS. 1A and 1B show one embodiment of a probe. Probe 20 comprises a carrier having a longitudinal axis 22 extending between a first terminal end 24, which is inserted into the patient's body, and a second terminal end, not shown, which remains outside of the patient's body. Extending through the carrier is a smaller diameter conduit 26, called a lumen, through which surgical tools, such as a biopsy needle 28, can be transmitted from outside of the patient's body to a recess area 30 near the first terminal end 24. Typically, such a carrier for a laparoscopic probe would have a maximum cross sectional width smaller than about 12 millimeters, and often from about 10 millimeters to about 12 millimeters.

The probe 20 also has an array 32 of ultrasonic transducers comprising a curved first portion 34 and a linear second portion 36. The curved portion 34 has at least one ultrasonic transducer that is situated to image at an acute angle relative to the longitudinal axis 22. Preferably, the curved portion 34 comprises a plurality of ultrasonic transducer elements arranged in a planar curve. The curved portion 34 shown in FIG. 1A is configured as a planar curve having a 90° included angle and a radius of curvature 38, as shown.

The curved portion 34 is continuous with the linear portion 36, which has a plurality of ultrasonic transducer elements located substantially in a line that is substantially parallel to the longitudinal axis 22. The linear portion 36, therefore, produces an ultrasound image directed to the side of the probe. An array having a curved first portion extending over a 90° arc and a linear second portion, as shown in FIG. 1A, has an ultrasound imaging pattern 40 extending from a full forward imaging position at one end of the curved portion 34 to a full side imaging position along the linear portion 36.

The array 32 is preferably located relative to the lumen 26 so that a surgical tool, such as a biopsy needle 28, exiting the lumen 26 will pass through the recess area 30 in such a manner that the tool passes through the field of view of the linear portion 36 of the array. If the tool exiting the lumen 26 is extended through the recess beyond the linear portion 36, such tool would also preferably pass within the field of view of the curved portion 34 of the array. This ability to pass surgical tools directly to the vicinity of the array 32 can facilitate precise placement of tools, such as biopsy needles, at the desired point as located by the ultrasonic image produced by the array 32.

Preferably, the array 32 has at least about thirty-two transducer elements, more preferably at least about sixty-four transducer elements, and most preferably at least about one hundred and twenty-eight transducer elements. The relative number of transducer elements included in the curved portion 34 relative to the linear portion 36 will depend upon the specific embodiment and the relative needs for viewing beyond the first terminal end of the carrier and viewing to the side of the carrier. Frequently, however, transducer elements will be equally split between the two portions. Transducer elements are typically from about 3 mm to about 5 mm long. The individual transducer elements can be spaced at any convenient distance from each other, providing that spacing is close enough to provide adequate imaging. Frequently, transducer elements are spaced from about 0.1 mm to about 0.3 mm on center and preferably at about 0.2 mm on center, with the longitudinal axis of the transducer elements extending into the internal space of the carrier. An array with one hundred twenty-eight transducers would, therefore, be approximately one inch long as measured along the surface of the array.

Viewing beyond the first terminal end of the probe using the curved array portion 34 is desirable to help determine what organs or other tissue lie in the path of the probe, to help determine when the probe has reached the proper distance into the patient's body, and to identify organs or tissue of interest. The side looking second portion 36 is particularly suited for viewing a particular organ or other tissue once the probe has been positioned at the proper distance within the patient's body.

Figure 2A:
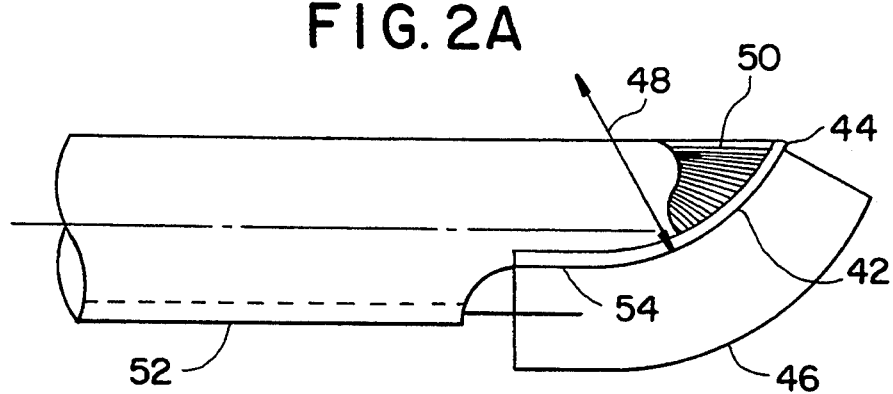
FIGS. 2A and 2B show a side view and end view of a probe having both a curved first array portion and a linear second array portion of an ultrasonic transducer array, with the curved first array portion included within an acute angle and having an enlarged radius of curvature to facilitate the making of electrical connections to individual transducer elements.
Figure 2B:
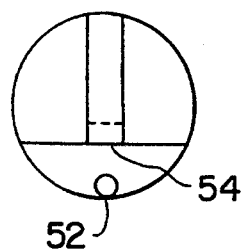

FIGS. 2A and 2B show another embodiment of a laparoscopic ultrasonic probe having features as previously described for the probe shown in FIGS. 1A and 1B, except as noted. The first portion 42 of the ultrasonic transducer array is shown as arranged in a planar curve having a larger radius of curvature than that shown in FIGS. 1A and 1B. Also, the curved portion 42 has an acute included angle. Therefore, the curved first portion 42 has a capability of imaging, as shown by the imaging pattern 46, beyond the end of the probe that is somewhat restricted relative to the 90° curved first portion 34 shown in FIG. 1A. The relatively flatter curve of the curved portion 42 relative to that shown in FIG. 1A is due to the larger radius of curvature 48 that extends well beyond the edge of the probe carrier, as shown.

The relatively flatter curve in the arc of curved portion 42, although somewhat reducing the forward viewing capability of the array, has the advantage of facilitating electrical connection of transducer wires 50 to individual transducer elements in the curved first array portion 42. Such additional space for making electrical connections to individual transducer elements can significantly decrease the cost of manufacturing the probe. As an alternative to a larger radius of curvature, an increasing radius of curvature can also be used. For example, the radius of curvature of the curved array portion could be smallest at the end of the curved portion nearest the end of the probe and could increase, thereby flattening the curve, moving along the curved portion away from the end of the probe.

The probe shown in FIGS. 2A and 2B also has a lumen 52 extending through the carrier and through which surgical tools can be transmitted to a recessed area in the vicinity of the linear second array portion 54.

Figure 3:
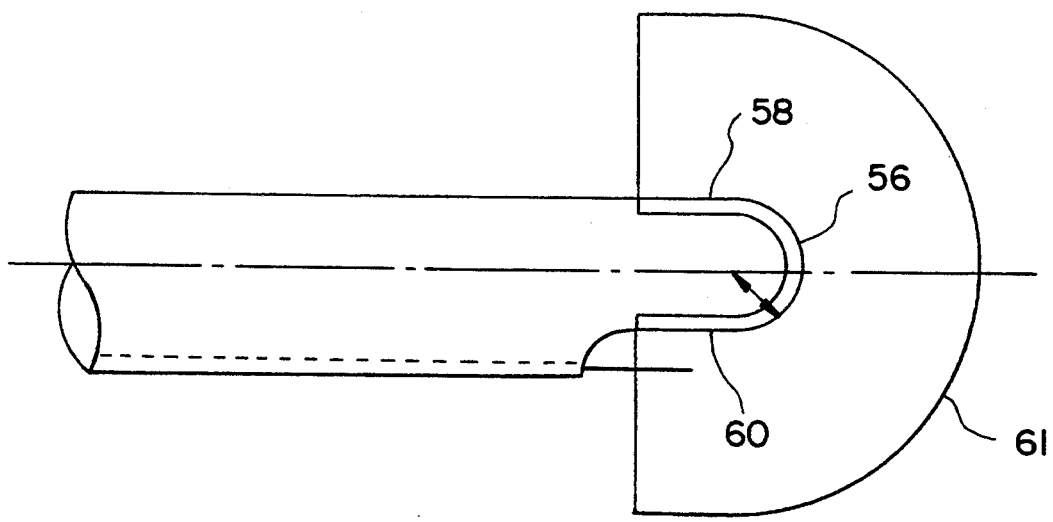
FIG. 3 shows a side view of a probe having an ultrasonic transducer array comprised of a 180° curved first array portion and two linear array portions.

FIG. 3 shows another embodiment of an ultrasonic probe for use in laparoscopic surgery. The first portion 56 of the array extends over a full semi-circle. Other configurations for the first portion that extend from one side of the probe to the other are also possible, and need not extend through a full 180°. Unlike the probes previously described, this probe contains two linear portions 58 and 60, thus providing an imaging pattern 61 extending down two sides of the probe and completely around the front of the probe.

Another aspect of the present invention involves sensing the position of an ultrasonic probe, generating an electrical signal representative of the position of the probe, and using that electrical signal to orient a video display of an ultrasonic image generated by the probe.

Figure 4:
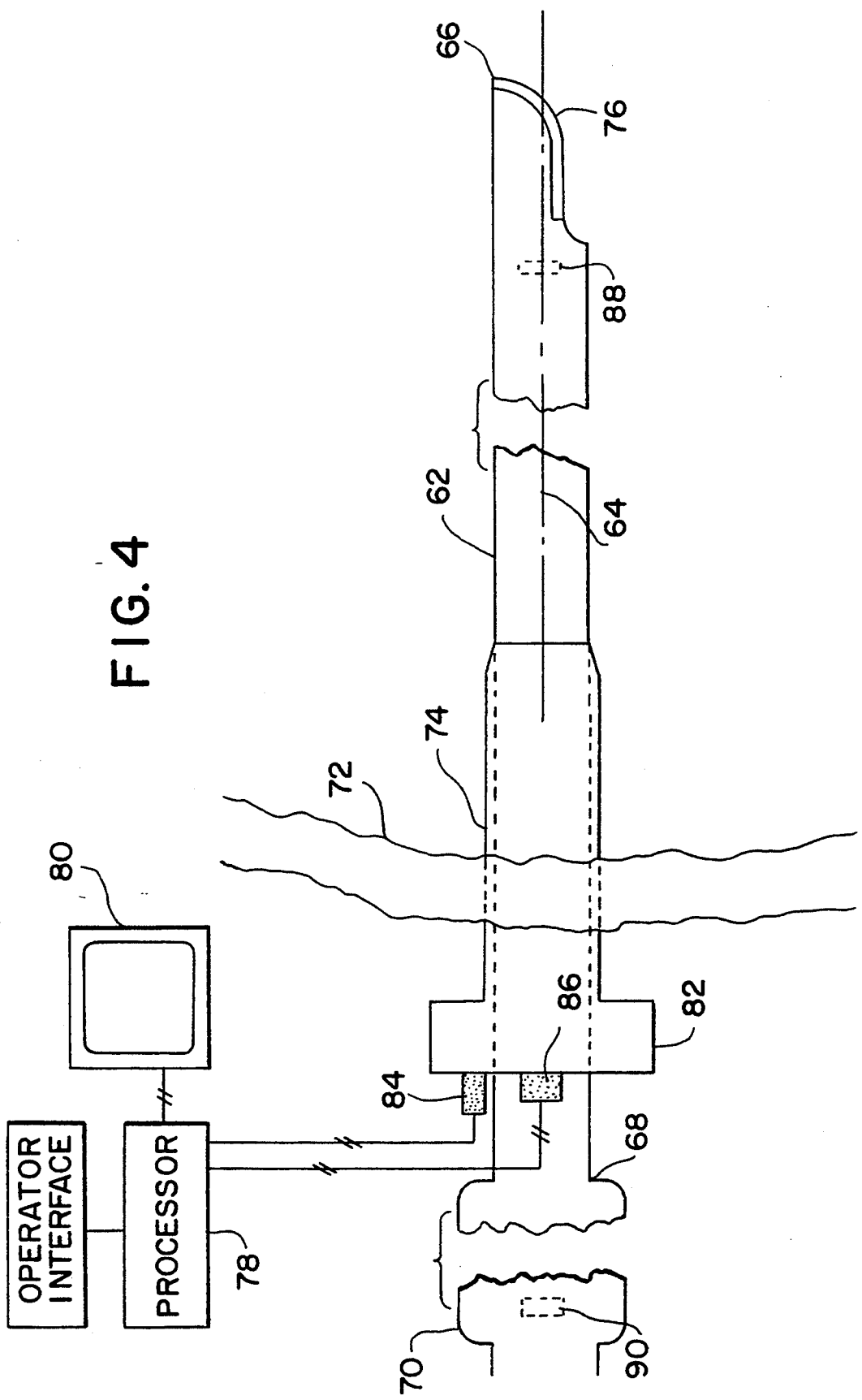
FIG. 4 shows an apparatus for use in performing ultrasonic imaging that includes translational and rotational position sensing devices for sensing the position of an ultrasonic probe and using the position information to manipulate the displayed ultrasonic video image.

FIG. 4 shows one embodiment of the invention. An ultrasonic probe 62 with a longitudinal axis 64 having a first terminal end 66 that is inserted into a patient's body and a second terminal end 68 that is connected to a handle 70, with which a surgeon would manipulate the probe. The first terminal end 66 of the probe is inserted into the patient's body through a hole in the abdominal cavity 72 that is held open by a tubular device 74, called a cannula, the internal passageway through which is often referred to as a surgical port. An array 76 having a plurality of ultrasonic transducers is located near the first terminal end 66 of the probe. The ultrasonic transducers produce first electrical signals that are applied to a processor 78 that places the signals in a form suitable for display as a video ultrasound image on a video monitor 80. Electrical circuits for the ultrasound transducers are not shown.

Mounted on the cannula adjacent to the surgical port are two position sensors 84 and 86. A first position sensor 84 monitors the translational position of the probe 62 along the longitudinal axis 64. A second position sensor 86 monitors the rotational position of probe 62 about the longitudinal axis 64.

The first positional sensor 84 generates an electrical signal representative of the translational position of the probe which goes to a processor 78 and is used to manipulate ultrasound video images formed from the signals provided by the array 76. For example, the electrical signal provided by the first positional sensor 84 can be used to generate consecutive video ultrasound images to be displayed sequentially across the video monitor in proper spacial relationship to one another in a translational direction.

The second position sensor 86 generates an electrical signal that is representative of the rotational portion of the probe which is transmitted to a processor 78 where the signal is used to manipulate and orient an ultrasound video image formed from the signals provided by the array 76 relative to the rotational position of the array 76 on the probe 62. For example, if the array 76 is imaging at a first position and is subsequently rotated to a second position in a counterclockwise direction, the ultrasound video image on the monitor 80 also rotates on the video monitor screen in a counterclockwise direction.

In one embodiment, a reference point can be set so that a particular direction on the video monitor represents a specific orientation relative to the patient. For example, if a probe is inserted through the surgical port and travels in a vertical direction into the body cavity, it may be desirable to select the top of the video monitor as corresponding to the head of the patient. If the ultrasonic array is then rotated to image in a direction towards the head, the portions of the image closest to the ultrasonic array will appear at the bottom of the video monitor and the portions of the image farthest from the array, being closer to the head, will appear at top of the video monitor. If the probe is then rotated to image in a direction towards the feet, then those portions of the image closest to the probe will be near the top of the video monitor and those portions of the image farthest from the probe will appear near the bottom of the video monitor. If the probe is positioned to look to one side, or the other, of the patient's body then portions of the image closest to the array would show near the appropriate side of the monitor.

If, however, a surgeon is inserting a probe through a surgical port that enters the body mostly from the side such that the probe travels across the body cavity, then it might be convenient for the surgeon to select the top of the screen as corresponding to the front the patient's body. The bottom of the screen would correspond to the back of the patient's body. The video image would rotate as the probe rotates, but the video image would always maintain orientation relative to the front and back of the patient, similar to orientation with the head and feet as previously described.

Positional sensors 84 and 86 can be any devices that produce electrical signals indicative of the position of the probe 62. For example, these sensors might have friction wheels that contact the probe 62 and that are coupled to opto-electronic encoders or counters that produce electrical signals. Another method of sensing position might be to put a series of dots, lines, or other marks directly on the shaft of the ultrasound probe 62 and to optically detect the motion of these marks using reflective encoders as position sensors 84 and 86.

In addition, or alternatively, to rotational position sensor 84, which is mounted at the surgical port, a rotational sensor that is sensitive to gravitational force could be placed within the probe. Preferably, such a gravitationally sensitive sensor 88 would be positioned near the first terminal end in the vicinity of the array 76. Alternatively, such a gravitationally sensitive sensor 90 could be placed in the handle 70 attached to the probe 62.

Figure 5:
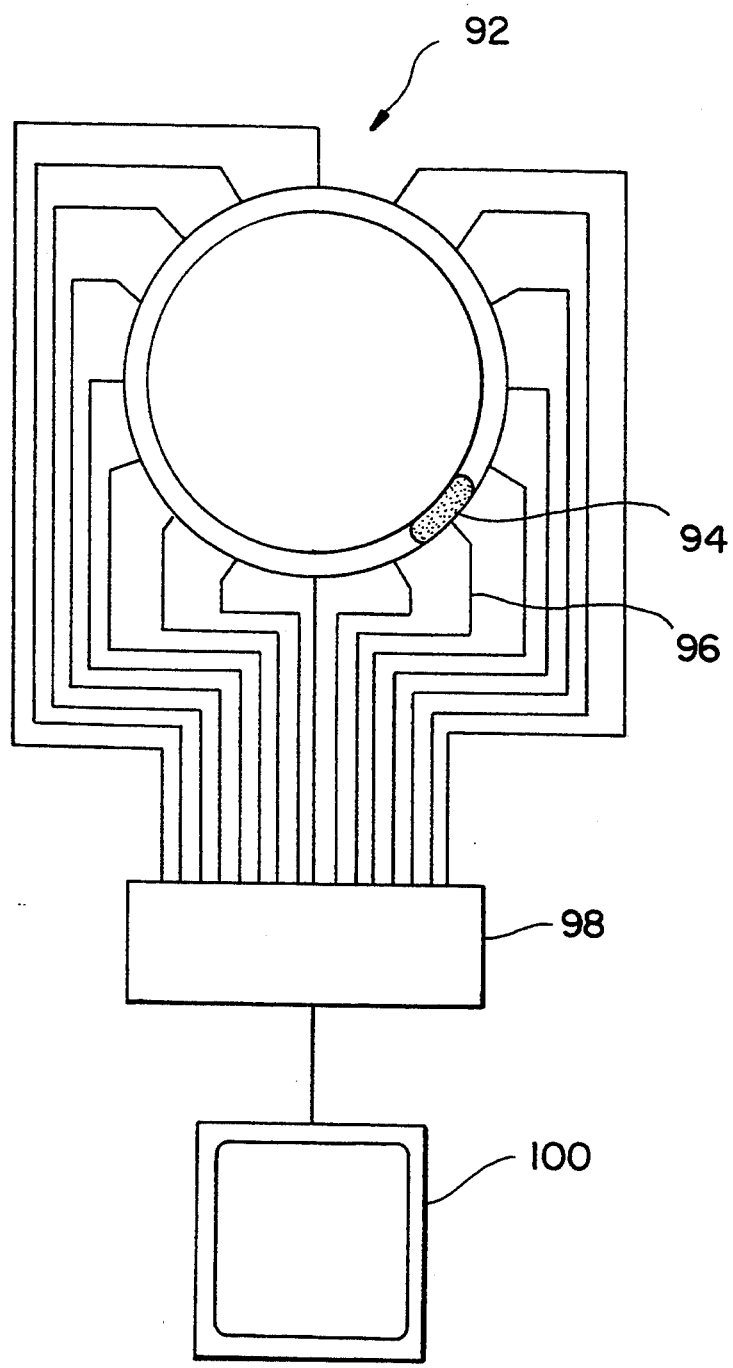
FIG. 5 shows a mercury switch that can be used to sense rotational position of a probe based on gravitational force.

One suitable gravitationally sensitive position sensor is a switch having an electrically conductive mass, such as a ball of liquid mercury or a solid metal ball, that is capable of responding to gravitational force to close one of several contacts in the switch. FIG. 5 shows a switch 92 actuated by a ball of mercury. As a probe with the mercury switch 92 is rotated, a ball of mercury 94 in mercury switch 92 moves such that the mercury is always at the position of the switch pointing in a downward direction in response to the gravitational force. The mercury switch will, therefore, complete the circuit with the contact that is pointing down and an electrical signal will be generated in the circuit completed by the contact and the electrical signal is transmitted to a processor 98 where it is used to orient an ultrasonic video display on video monitor 100. Rotation of the ultrasound video image is as described previously for rotational position sensor 84 as shown in FIG. 4.

As previously discussed, a reference point can be established for orientation of a video ultrasound image relative to the patient. The reference point for the position sensors can be established in either an absolute or a relative sense. For example, if a rotational position sensor is used that responds to gravity, then image orientation can be established with respect to actual up/down orientation. If however, the position sensor consists of either an optical or mechanical encoder, then in order to establish a reference position, the system operator would have to move the probe into a predetermined position (i.e., image plane from front to back) and then notify the system by means of a switch or contact closure, via an operator interface 101 with processor 78, that the probe is in the reference position.

In a further aspect, the present invention provides a probe for internal use in medical operations, and particularly for use with laparoscopic surgery, that includes both a surgical device and an ultrasonic device with a field of imaging that either includes the surgical device or is immediately adjacent to the surgical device. In one embodiment, the surgical device is a tool designed for cutting and/or cauterizing tissue, such as, for example an electrocautery hook, a laser, or an ultrasonic cutter. Combining a surgical device in close proximity with an ultrasonic device on a probe is particularly advantageous when the surgical device is designed to cut and/or cauterize tissue, because the combination provides close control of the cutting operation to assure that only the intended tissue is actually cut and/or cauterized.

Figure 6:
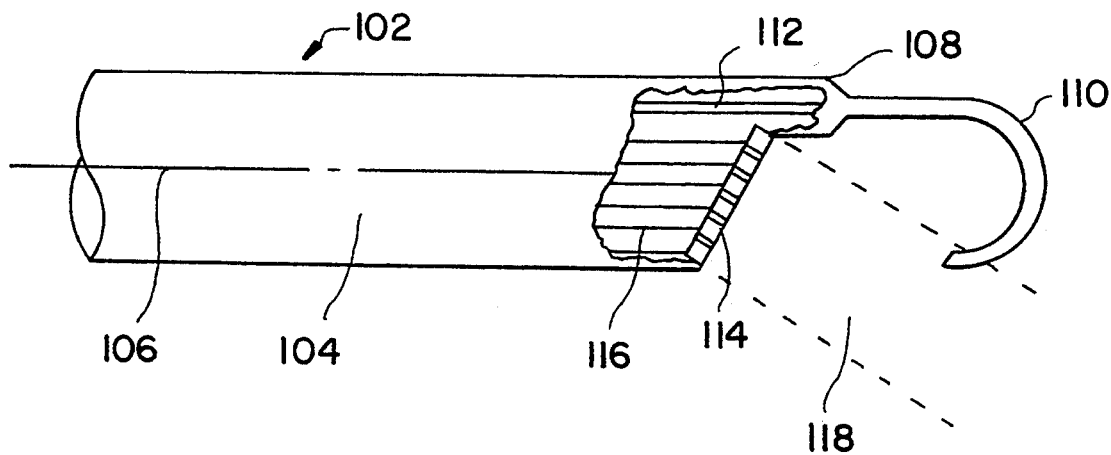
FIG. 6 shows a probe having an ultrasonic transducer array and an electrocautery hook located partially within the field of imaging of the array.

FIG. 6 shows one embodiment comprising an electrocautery hook. The probe 102 has a carrier 104 with a longitudinal axis 106 extending between a first terminal end 108 that enters into a patient's body and a second terminal end, not shown, that remains outside of the patient's body. Mounted at the first terminal end 108 is an electrocautery hook 110 that is connected to electrical wires 112 that supply electricity to the electrocautery hook to provide the required thermal energy for cutting and/or cauterizing tissue. Also mounted near the first terminal end is an array 114 having a plurality of ultrasonic transducer elements connected to electrical wires 116 that transmit electrical signals that are representative of an ultrasonic signal received by the array 114 that can be processed and displayed on a video monitor.

The ultrasonic transducer array 114 is mounted on the carrier in such a manner that the field of imaging includes the tip of the electrocautery hook 110. Therefore, a surgeon using such a probe would be able to simultaneously view the tissue to be cut and the tip of the electrocautery probe. The surgeon would, therefore, have a high degree of control in assuring that only the proper tissue is cut.

In some instances, it may be desirable to have improved side imaging capabilities. In such cases, it may be desirable to orient the field of imaging such that it does not actually include the surgical device, but is adjacent to the surgical device in such a manner that the surgeon can carefully control the location and operation of the surgical device to assure that the proper operation is performed. In some applications, it will be desirable to combine forward and side imaging capabilities using an ultrasonic transducer array combining both forward and side imaging features as previously discussed.

In yet a further aspect, the present invention provides an apparatus, such as a probe useful in laparoscopic surgery, and a method for establishing an ultrasonic circuit to facilitate ultrasonic imaging of body tissue of interest. The apparatus comprises a carrier, an ultrasonic device mounted on the carrier, and means for injecting an ultrasonically transmissive medium adjacent to the ultrasonic device.

Figure 7:
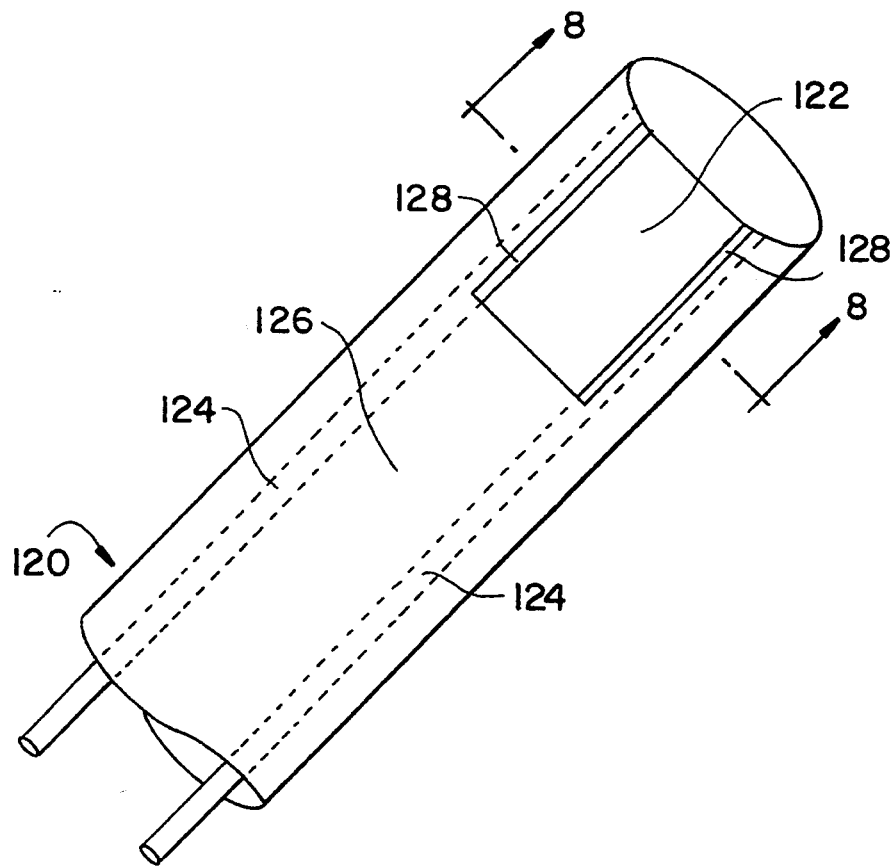
FIG. 7 shows a laparoscopic probe having an ultrasonic array and lumens for injecting transmissive fluid in the vicinity of an ultrasonic transducer array.
Figure 8:
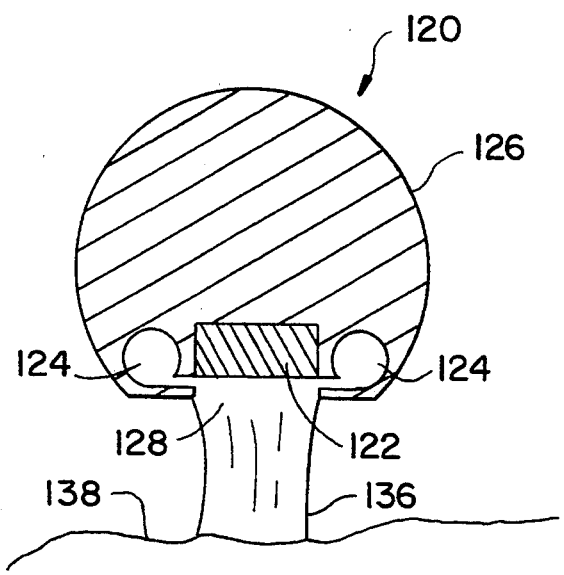
FIG. 8 shows a cross section of a probe having means for injecting transmissive fluid adjacent to an ultrasonic transducer array.

FIGS. 7 and 8 show a probe 120 having an array 122 of ultrasonic transducers and two lumens 124 passing through the carrier 126. The lumens 124 are used to transmit an ultrasonically transmissive medium 136 to openings 128 adjacent to the array 122 of transducer elements.

In the case of laparoscopic surgical operations, the probe 120 would be inserted into the patient's body and moved to a position as close as possible to tissue 138 of interest for the purpose of obtaining an ultrasonic image of that tissue. To establish, or to improve, ultrasonic contact between ultrasonic transducers of the array 122 and the tissue 138 of interest, an ultrasonically transmissive fluid is injected through the lumens 124 such that the ultrasonically transmissive fluid exits from openings 128 adjacent to the transducer array 122. Consequently, the ultrasonically transmissive fluid can establish an ultrasonic circuit between the array 122 and tissue 138 in the field of view of the array.

The transmissive medium can be any substance that is ultrasonically transmissive and capable of being injected through the lumens 124. Although water is ultrasonically transmissive, in one embodiment a higher viscosity fluid is used to reduce the tendency of the transmissive medium to disperse or flow away from the immediate vicinity of the transducer array 122. In one embodiment, a high viscosity fluid that has a viscosity of greater than about 20,000 cP and preferably from about 20,000 cP to about 80,000 cP. One suitable high viscosity fluid include, for example, is sodium hyaluronate, having a viscosity of approximately 40,000 cP. Preferably, the high viscosity fluid, after being injected through the openings 128, adheres to the surface of the transducer 122 array and to the carrier 120 in the immediate vicinity, thereby forming an ultrasonically transmissive circuit between the transducer array 122 and the tissue 138 in the field of view of the transducer array 122 with little, if any, of the high viscosity fluid dispersing or flowing away from the area in the immediate vicinity of the transducer array and the tissue of interest. After imaging of tissue of interest is complete, the high viscosity fluid can be removed by applying suction to the lumens 124.

In one aspect, the present invention provides a disposable sheath for covering a probe, particularly for covering a laparoscopic probe having an ultrasonic device. The sheath covers the probe, thereby reducing or eliminating the need to sterilize the probe after use. The sheath covers the probe and extends from at least the terminal end of the probe that is inserted into the body cavity to a point on the probe that remains outside of the body cavity at all times. Preferably, the sheath covers the entire length of the probe.

Figure 9A:
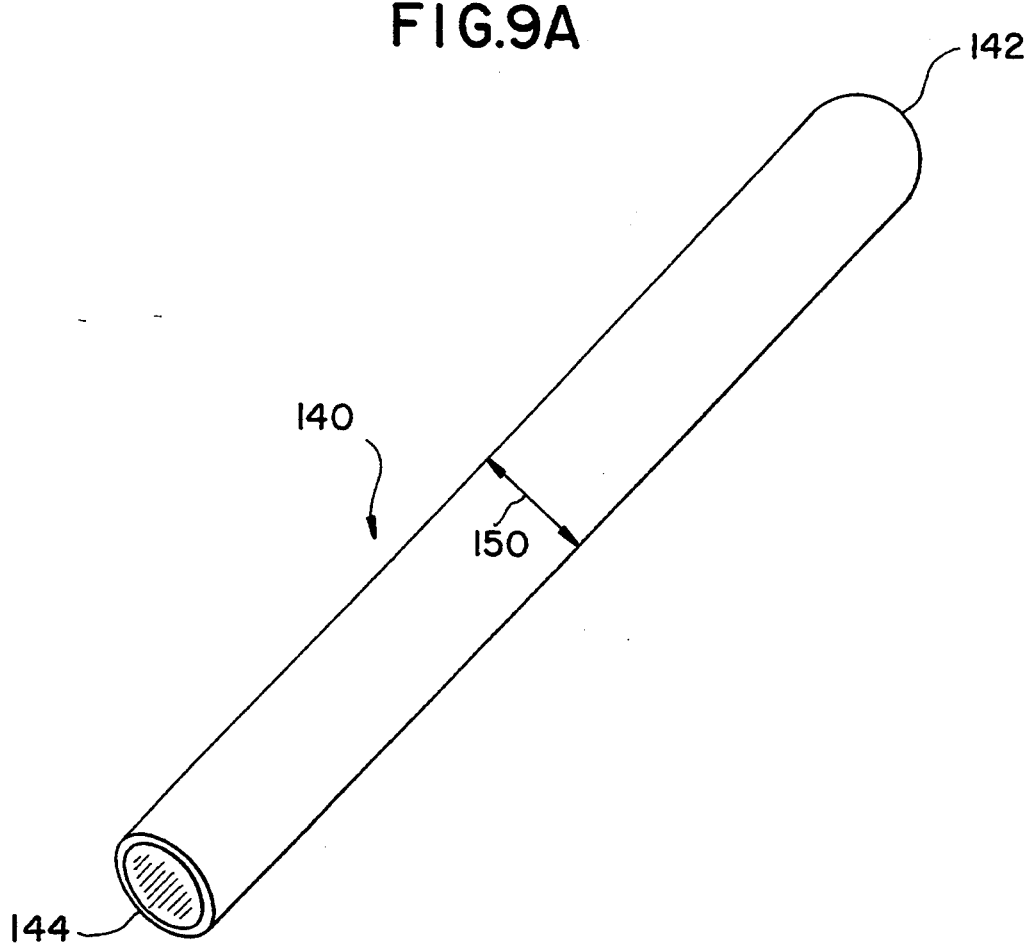
FIGS. 9A and 9B show a perspective view and a cross sectional view along the longitudinal axis of a first embodiment of a rigid sheath.
Figure 9B:
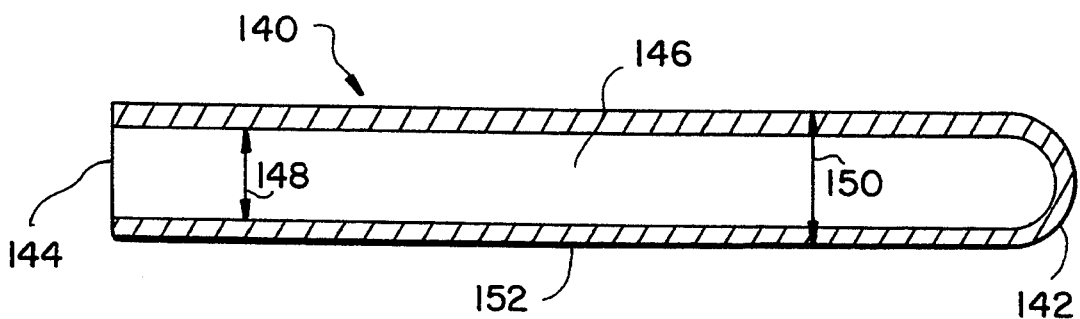

FIGS. 9A and 9B show a perspective view and a cross sectional view along the longitudinal axis of a rigid sheath 140 that is of a tubular shape designed to cover a generally tubular shaped laparoscopic probe having an ultrasonic device. The rigid sheath 140 has a first terminal end 142 that is inserted into a patient's body cavity along with the probe and a second terminal end 144 that remains outside of the body at all times. To cover a laparoscopic probe with the rigid sheath 140, the probe is inserted into the internal, hollow space 146 of the sheath.

The rigid sheath 140 is preferably shaped to provide a close fit to the probe to be covered. Therefore, a tubular shaped sheath should be used to cover a tubular probe. Also, the fit between the laparoscopic probe and the rigid sheath should be of a close tolerance. Preferably, the maximum outside diameter of a tubular probe to be inserted into a tubular sheath should be not more than about 0.15 mm smaller than the internal diameter 148 of the rigid sheath 140.

The sheath 150, is preferably keyed with and latched to the probe inserted into the sheath in any fashion that prevents the sheath and the inserted probe from moving relative to one another during use of the probe. For example, the portion of probe, or the probe handle, which remain outside of the body during use could have a protrusion that corresponds to a keyed slot or recess in the sheath. The protrusion could also be spring actuated, for example, to latch into a recess in the sheath, thereby preventing the sheath and probe from moving relative to one another in either a rotational or translational direction.

The outer diameter 150 of the rigid sheath is smaller than the inside diameter of a cannula or surgical port. Preferably, the outer diameter 150 of the rigid sheath is not more than about 0.15 mm smaller than the diameter of the surgical port, being defined by the inner diameter of the smallest restriction through the cannula.

The rigid sheath 140 has a thin wall 152 that is preferably no greater than about 0.4 mm in thickness. The rigid sheath 140 can be made of any material, or combinations or composites of materials, that either alone or in combination with the tubular shape of the sheath provide the desired rigidity. By rigidity, it is meant that the structure of the sheath is such that material of the sheath will not bunch up, such as in folds, as would be experienced with a thin-walled, highly flexible sheath made of elastomeric-type material such as latex rubber, which can be sterilized. Rather, the rigid sheath 140, is a generally self-supporting structure that resists such bunching of the material of the sheath. Therefore, the rigid sheath 140 reduces, or substantially eliminates, the binding problem associated with insertion and extraction of a probe covered by a sheath into and out of a patient's body through the cannula. Suitable materials for manufacture of the rigid sheath include, for example, metals, including steel, and relatively nonelastic polymeric compositions, such as those containing polycarbonates or polyethylenes. Polycarbonate-based compositions are particularly preferred because of the high biocompatibility and transparency of polycarbonates. Although transparency is not required, it is desirable so that the fit of the probe into the sheath can be observed at the time the probe is covered by the sheath.

Figure 10A:
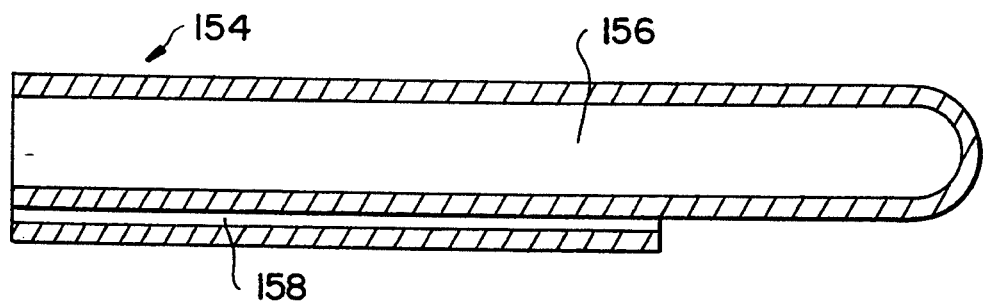
FIGS. 10A and 10B show a cross section along the longitudinal axis and a cross section perpendicular to the longitudinal axis of a second embodiment of a rigid sheath that also has a lumen that can be used for various purposes.
Figure 10B:
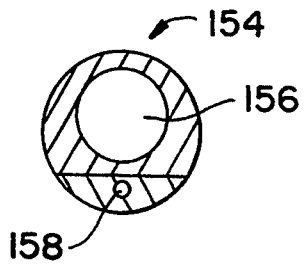

FIGS. 10A and 10B show a cross sectional view along the longitudinal axis and a cross sectional view perpendicular to the longitudinal axis of a second sheath 154 having a first interior, hollow space 156 in which a probe can be inserted prior to entry into a body cavity and second interior, hollow space 158 that is a lumen useful for transmitting fluids or surgical tools, such as a biopsy needle, to the area adjacent to the end of the probe, such as near the ultrasound imaging area of the probe. The sheath 154 is preferably a rigid sheath, as previously described.

Figure 11:
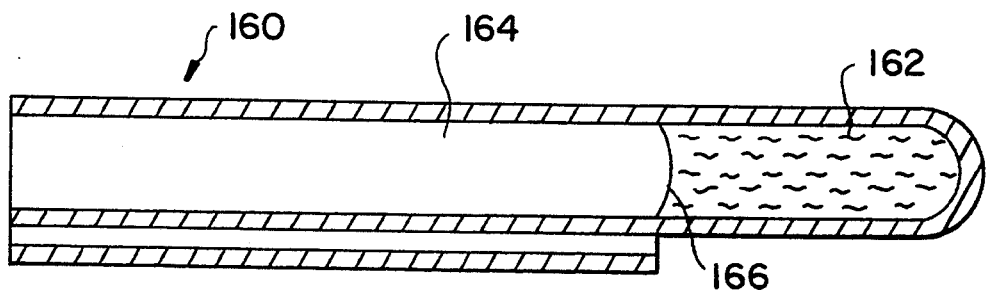
FIG. 11 shows another embodiment of the sheath having a chamber filled with transmissive medium and sealed with a breakable membrane.

FIG. 11 shows a third sheath 160 that is similar to the sheath previously described and shown in FIGS. 10A and 10B, except that the sheath 160 has a chamber 162 that contains an ultrasonically transmissive medium, such as a viscous fluid or deaerated water. The chamber is sealed and partitioned from other interior space of the sheath 164 by a thin membrane 166. The thin membrane 166 may be manufactured from any suitable material that is capable of sealing the chamber 162, but that can be pierced and ruptured by applying force to the membrane, such as by forcing a probe inserted into the sheath against and through the membrane 162. Suitable materials for manufacturing of the membrane 166 include, for example, polyethylene and polyvinyl chloride films.

FIG. 12 shows the same sheath 160, but after the thin membrane 166 has been broken by insertion of an ultrasonic probe 170. Upon breaking the thin membrane 166, the probe is forced into the chamber 162 such that the transducer device of the probe is surrounded by ultrasonically transmissive medium that forms an ultrasonic circuit between the ultrasonic device and the sheath 160.

FIG. 13 shows a fourth sheath 172 having attached at the terminal end, which enters into the body cavity, a balloon 174 that is made of an elastomeric-type material, such as latex rubber. The balloon 174 is in fluid communication with both the interior space 176 in which a probe can be inserted and a lumen 178 through which transmissive medium can be injected to inflate the balloon 174. The sheath 172 also has a sealing device 180 for sealing around the outer surface of a probe inserted through the sealing device 180. Such a sealing device could be, for example, an o-ring, chevron seals, or the like.

FIG. 14 shows the same sheath 172 in which an ultrasonic probe 182 has been inserted. The probe 182, as shown, has been inserted through the sealing device 180 to form an annular seal about the outer surface of the probe 182. The balloon 174 has been inflated by the injection of ultrasonically transmissive medium through lumen 178, such that the ultrasonic device of probe 182 is surrounded by ultrasonically transmissive medium that establishes an ultrasonic circuit between the ultrasonic device and the balloon 174. By contacting the balloon with tissue of interest, an ultrasonic circuit can be established between the tissue and the ultrasonic probe. Also, the standoff distance provided between the inflated balloon and the ultrasonic device can significantly enhance ultrasound imaging.

Figure 15:
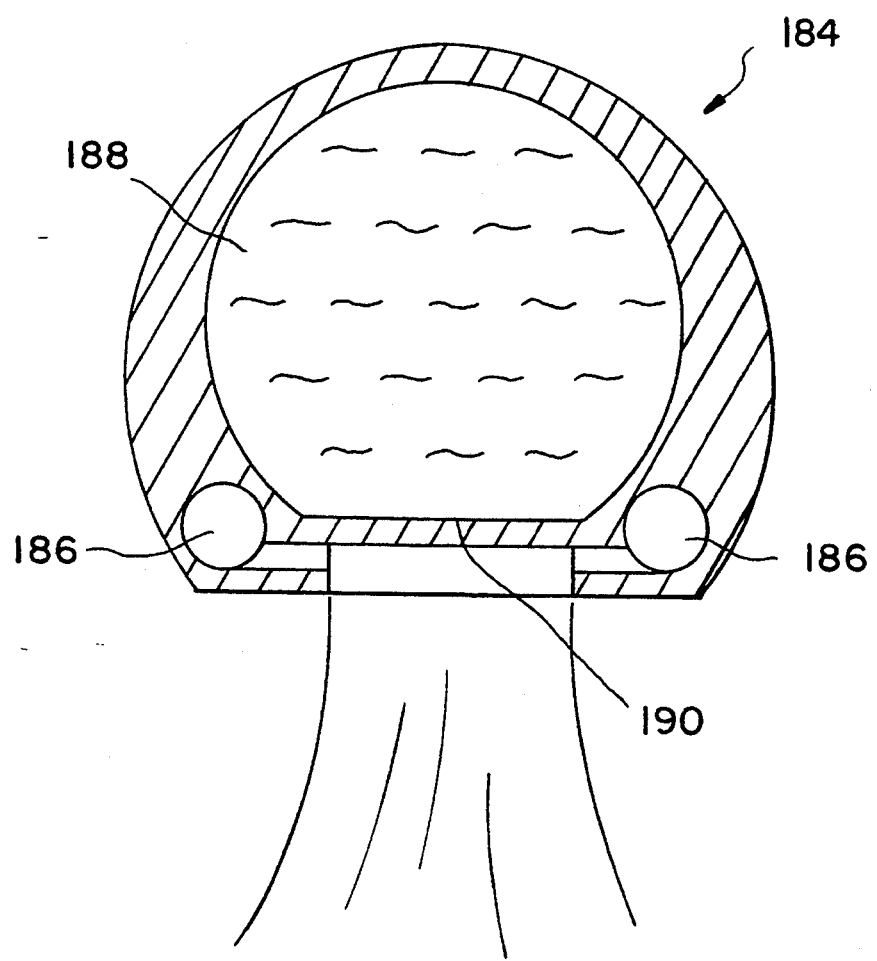
FIG. 15 shows a cross section of a sheath having lumens for placing transmissive medium in a area to be ultrasonically imaged.

FIG. 15 shows a cross section that is perpendicular to the longitudinal axis of a fifth sheath 184. The sheath 184 has two lumens 186 through which ultrasonic medium can be transmitted to and injected adjacent to the sheath, preferably at a distance along the longitudinal axis of the sheath corresponding to the position of an ultrasonic device on a probe inserted into the sheath. Preferably, ultrasonic medium injected through lumens 186 establishes an ultrasonic circuit between the sheath 184 and tissue of interest to be ultrasonically imaged. Preferably, a probe inserted into sheath 184 is positioned such that an ultrasonic device on the probe would be situated at a distance along the sheath's longitudinal axis that corresponds with the area where ultrasonic medium injected through lumens 186 would exit the sheath.

Suitable transmissive medium, would be any medium capable of transmitting ultrasound images, as previously discussed. In one case, the ultrasonically transmissive medium would be a high viscosity fluid that would adhere to the sheath following injection from lumens 186 in such a manner that the ultrasonically transmissive medium would not disperse or flow away from the sheath 184, and therefore, could be readily removed by suction through lumens 186 following ultrasound imaging.

Additionally, to establish an ultrasonic circuit between the ultrasonic device of a probe inserted into the sheath 184 and the sheath 184, an ultrasonically transmissive medium could be placed inside the interior space 188 of sheath 184.

The shape of sheath 184 is preferably designed so that the shape of the probe to be inserted into the sheath 184 and the shape of the sheath 184 are keyed so that the inserted probe and sheath can be rotated as a unit with the ultrasonic device of the probe correspondingly located to the position of the sheath 184 where ultrasonically transmissive medium may be injected through the lumens 186. For example, flat surface 190 of the sheath 184 could be keyed to a close tolerance probe design also containing a corresponding flat surface which contains an ultrasonic device.

Any aspect of the invention can be combined in any way with other aspects. Any of the features of probes shown in FIGS. 1A, 1B, 2A, 2B, 3, 6, 7 and 8 can be combined with image orientation and translation, as shown in FIG. 4, and/or any of the sheaths shown in FIGS. 9A, 9B, 10A, 10B, 11, 12, 13, 14 and 15, making appropriate modifications, as necessary. For example, a probe having a curved array portion and a linear array portion could be inserted into a rigid sheath having an electrocautery probe attached to the sheath with electrical wires to operate the sheath passing through a lumen attached to the sheath.

The foregoing description of the invention has been presented for purposes of illustration and description. Further, the description is not intended to limit the variations and modifications commensurate with the above teachings, and the skill or knowledge in the relevant art are within the scope of the present invention. The preferred embodiment described hereinabove is further intended to explain the best mode known of practicing the invention and to enable others skilled in the art to utilize the invention in various embodiments and with the various modifications required by their particular applications or uses of the invention. It is intended that the appended claims be construed to include alternate embodiments to the extent permitted by the prior art.

What is claimed is:

1. A medical ultrasonic imaging apparatus that provides both forward-looking and side-looking imaging capability comprising:
   a carrier that is adapted for insertion into a body cavity, said carrier has a first terminal end that is inserted into the body cavity during use of the apparatus, a second terminal end that remains outside of the body cavity during use of the apparatus, and a longitudinal axis that extends between said first terminal end and said second terminal end of said carrier; and
   an array of ultrasonic transducers, operatively attached to said carrier, for receiving ultrasonic signals from the areas forward of said first terminal end of said carrier and to the side of said carrier and generating electrical signals that are representative of the received ultrasonic signals and can be used to construct an ultrasonic image of the tissue adjacent to said array of ultrasonic transducers, said array of ultrasonic transducers includes a first array portion for contributing to the production of an ultrasonic image of the area forward of said first terminal end of said carrier and a second array portion for contributing to the production of an ultrasonic image of the area to a side of said carrier, said first array portion includes at least one transducer that is oriented at an acute angle of less than 90° as measured from the line of said longitudinal axis of said carrier, and said second array portion includes at least two transducers that are oriented relative to one another in a substantially straight line, a first of said at least two transducers located closer to said first terminal end than a second of said at least two transducers.

2. An apparatus, as claimed in claim 1, wherein:

said first array portion includes a plurality of transducers that are oriented with respect to one another so as to define a curve.

3. An apparatus, as claimed in claim 1, wherein:
said first array portion includes a plurality of transducers that are oriented with respect to one another so as to define a planar curve.

4. An apparatus, as claimed in claim 1, wherein:
said first array portion includes a plurality of transducers that are oriented with respect to one another so as to define a planar curve, said second array portion includes a first linear array portion and a second linear array portion, said first linear array portion including a plurality of transducers that are oriented relative to one another in a substantially straight line, said second linear array portion including a plurality of transducers that are oriented relative to one another in a substantially straight line, the substantially straight lines of said first linear array portion and said second linear array portion being substantially parallel to said longitudinal axis of said carrier and being located on substantially opposite sides of a plane that includes said longitudinal axis, said substantially straight lines of said first linear array portion and said second linear array portion and said planar curve of said first array portion all being within a single plane.

5. An apparatus, as claimed in claim 1, wherein:
said first array portion includes a plurality of transducers that are oriented with respect to one another to define a planar curve and have a field of view that is less than 90°.

6. An apparatus, as claimed in claim 1, wherein:
said first array portion includes a plurality of transducers that are oriented with respect to one another to define a planar curve, transducers of said first array portion that are located at different positions on said planar curve each being at different distances from said first terminal end, said curve having at any point on said curve a radius of curvature, said radius of curvature being smaller at points on said planar curve nearer said first terminal end than the radius of curvature at points on said planar curve further from said first terminal end.

7. An apparatus, as claimed in claim 1, wherein:
said carrier includes a surgical tool.

8. An apparatus, as claimed in claim 7, wherein:
said surgical tool is one of the following: located and capable of being located so as to be in the field of view of said second array portion.

9. An apparatus, as claimed in claim 7, wherein:
said carrier has a lumen extending longitudinally along said carrier and terminating some longitudinal distance from said first terminal end and in a direction towards said second terminal end, wherein at least a portion of said surgical tool is located in said lumen.

10. An apparatus, as claimed in claim 7, wherein:
said carrier has a lumen extending longitudinally along said carrier, said lumen terminating at an exit some longitudinal distance away from said first terminal end of said carrier in a direction towards said second terminal end, said surgical tool is one of the following: located past said exit and capable of being located past said exit of said lumen such that said surgical tool is within the field of view of said second array portion.

11. An apparatus, as claimed in claim 10, wherein:
said carrier in the vicinity of said first terminal end has a cross-sectional area that is substantially circular in peripheral shape, said lumen being located within said cross-sectional area.

12. An apparatus, as claimed in claim 7, wherein:
said carrier has a first cross-sectional area spaced longitudinally some distance away from said first terminal end in the direction of said second terminal end, said first cross-sectional area being greater than a second cross-sectional area of said carrier located closer to said first terminal end than said first cross-sectional area, said first cross-sectional area comprising a first cross-sectional portion that is intersected by said longitudinal axis and which comprises greater than 50 areal percent of said first cross-sectional area, said first array portion and said second array portion being located within said first cross-sectional portion, said first cross-sectional area comprising a second cross-sectional portion which is not intersected by said longitudinal axis of said carrier, and which comprises less than 50 areal percent of said first cross-sectional area, said first cross-sectional portion and said second cross-sectional portion not overlapping, said surgical tool being positioned within said second cross-sectional portion.

13. An apparatus, as claimed in claim 12, wherein:
said second cross-sectional portion does not overlap the cross-sectional area of said carrier at said first terminal end.

14. An apparatus, as claimed in claim 7, wherein:
said array is located to only one side of said surgical tool.

15. An apparatus, as claimed in claim 1, wherein:
said first terminal end of said carrier has a maximum cross-sectional area and includes a surgical tool, said array of ultrasonic transducers and said surgical tool located within the bounds of said maximum cross-sectional area.

16. An apparatus, as claimed in claim 1, wherein:
said at least two transducers of said second array portion that are oriented in a substantially straight line are also oriented substantially parallel to the longitudinal axis of said carrier.

17. An apparatus, as claimed in claim 1, wherein:
said first array portion has a plurality of transducers that are oriented with respect to one another so as to define a planar curve that is within a single plane that is substantially parallel to the longitudinal axis of said carrier.

18. An apparatus, as claimed in claim 1, wherein:
said first array portion includes a plurality of transducers that are oriented with respect to one another to define a planar curve, wherein said planar curve has a changing radius of curvature.

19. An apparatus, as claimed in claim 1, wherein:
said first array portion has a plurality of transducers that are oriented with respect to one another so as to define a curve, said curve curving away from said first terminal end toward said second terminal end such that a first transducer on said curve of said first array portion is closer to said longitudinal axis of said carrier than a second transducer on said curve of said first array portion that is located farther from said first terminal end in the direction of said second terminal end than said first transducer.

20. An apparatus, as claimed in claim 1, wherein:
said first array portion includes a plurality of transducers, wherein a first of said plurality of transducers of said first array portion is located closer to said first terminal end than a second of said plurality of transducers of said first array portion.

21. An apparatus, as claimed in claim 1, wherein:
said first array portion has a plurality of transducers that are oriented with respect to one another so as to define a planar curve, said substantially straight line defined by said at least two transducers of said second array portion and said planar curve lying within a single plane.

22. An apparatus, as claimed in claim 1, wherein:
said first array portion has a plurality of transducers that are oriented with respect to one another so as to define a planar curve with a changing radius of curvature, said substantially straight line defined by said at least two transducers of said second array portion and said planar curve lying in a single plane.

23. An apparatus, as claimed in claim 1, wherein:
said first array portion includes a plurality of transducers oriented with respect to one another so as to define a curve, wherein all of said curve is closer to said first terminal end than said straight line of said second array portion.

24. An apparatus, as claimed in claim 1, wherein:
said first array portion is substantially continuous with said second array portion such that said array can be used to produce a substantially continuous ultrasonic image extending from areas imaged by said first array portion through areas imaged by said second array portion.

25. An apparatus, as claimed in claim 1, wherein:
said first array portion is substantially continuous with said second array portion such that said array can be used to produce a substantially continuous ultrasonic image extending from areas imaged by said first array portion through areas imaged by said second array portion, said array having a continuous field of view of at least 90 degrees.

26. An apparatus, as claimed in claim 1, wherein:
said array has at least 32 transducers.

27. An apparatus, as claimed in claim 1, wherein:
said carrier has a first cross-sectional area spaced longitudinally some distance away from said first terminal end in the direction of said second terminal end, said first cross-sectional area being greater than a second cross-sectional area of said carrier that is located closer to said first terminal end than said first cross-sectional area.

28. An apparatus, as claimed in claim 27, wherein:
said array is located substantially within said first cross-sectional area.

29. An apparatus, as claimed in claim 27, wherein:
said carrier includes a surgical tool that is located within said first cross-sectional area.

30. An apparatus, as claimed in claim 27, wherein:
said array and a surgical tool are both located within said first cross-sectional area.

31. An apparatus, as claimed in claim 27, wherein:
said array is located within said second cross-sectional area and a surgical tool is located within said first cross-sectional area.

32. An apparatus, as claimed in claim 27, wherein:
said array is located within said second cross-sectional area and a surgical tool is located within a portion of said first cross-sectional area that does not overlap with said second cross-sectional area.

33. An apparatus, as claimed in claim 27, wherein:
said array is located on a portion of said carrier having said second cross-sectional area.

34. An apparatus, as claimed in claim 1, further comprising:
a surgical tool for cutting and cauterizing tissue.

35. An apparatus, as claimed in claim 1, wherein:
said carrier includes a biopsy needle.

* * * * *